United States Patent
Yokosawa et al.

(10) Patent No.: US 10,058,509 B2
(45) Date of Patent: Aug. 28, 2018

(54) ALKYL CELLULOSE FOR USE IN TABLETING AND SOLID PREPARATION COMPRISING SAME

(71) Applicant: Shin-Etsu Chemical Co., Ltd., Tokyo (JP)

(72) Inventors: Takuya Yokosawa, Niigata-ken (JP); Naosuke Maruyama, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/622,354

(22) Filed: Jun. 14, 2017

(65) Prior Publication Data

US 2017/0273910 A1     Sep. 28, 2017

Related U.S. Application Data

(62) Division of application No. 14/880,755, filed on Oct. 12, 2015, now Pat. No. 9,713,593.

(30) Foreign Application Priority Data

Oct. 23, 2014  (JP) ................. 2014-216429

(51) Int. Cl.

| | |
|---|---|
| *C08B 11/08* | (2006.01) |
| *A61K 9/20* | (2006.01) |
| *C08B 11/20* | (2006.01) |
| *A61K 31/167* | (2006.01) |
| *C08B 11/02* | (2006.01) |

(52) U.S. Cl.
CPC .......... *A61K 9/2054* (2013.01); *A61K 9/2095* (2013.01); *A61K 31/167* (2013.01); *C08B 11/02* (2013.01); *C08B 11/20* (2013.01)

(58) Field of Classification Search
USPC .......................................................... 536/95
See application file for complete search history.

(56) References Cited

U.S. PATENT DOCUMENTS

| 8,519,120 B2 | 8/2013 | Maruyama | |
|---|---|---|---|
| 2007/0190017 A1* | 8/2007 | Yamasaki | C08J 3/12 424/76.1 |
| 2008/0039621 A1 | 2/2008 | Maruyama et al. | |
| 2012/0232167 A1 | 9/2012 | Takeuchi et al. | |
| 2014/0034760 A1 | 2/2014 | Takeuchi et al. | |
| 2014/0194618 A1 | 7/2014 | Narita | |

FOREIGN PATENT DOCUMENTS

| EP | 0 497 985 | 8/1992 |
|---|---|---|
| EP | 1 886 673 | 2/2008 |
| JP | 06-316535 A | 11/1994 |
| JP | 2010-254756 A | 11/2010 |
| WO | WO 2011/065350 A | 6/2011 |

OTHER PUBLICATIONS

"Chapter 2.53—Viscosity Determination", Japanese Pharmacopoeia 16th Edition; Mar. 24, 2011; pp. 67-69.
"Chapter 3.02—Specific Surface Area by Gas Adsorption", Japanese Pharmacopoeia 16th Edition; Mar. 24, 2011; pp. 84-86.
"Chapter 6.09—Disintegration Test", Japanese Pharmacopoeia 16th Edition; Mar. 24, 2011; pp. 135-136.
European Search Report for Corresponding European Application No. 15 187 406.2 dated Feb. 19, 2016.

* cited by examiner

*Primary Examiner* — Rei Tsang Shiao
(74) *Attorney, Agent, or Firm* — Alston & Bird LLP

(57) ABSTRACT

Provided are an alkyl cellulose excellent in formability when added even in a small amount and not causing marked delay in disintegration; a solid preparation comprising it; and a method for producing the solid preparation. More specifically, provided are an alkyl cellulose for use in tableting, the alkyl cellulose having a specific surface area of from 0.5 to 10.0 $m^2/g$ as measured by BET method and a solid preparation comprising the alkyl cellulose. Also provided is a method for producing the alkyl cellulose, comprising the steps of: bringing pulp into contact with an alkali metal hydroxide solution to obtain alkali cellulose, reacting the alkali cellulose with an etherifying agent to obtain a first alkyl cellulose, pulverizing the first alkyl cellulose, and depolymerizing the pulverized first alkyl cellulose through hydrolysis with an acid catalyst or through oxidative decomposition with an oxidant to obtain a second alkyl cellulose.

10 Claims, No Drawings

ALKYL CELLULOSE FOR USE IN TABLETING AND SOLID PREPARATION COMPRISING SAME

CROSS REFERENCE TO RELATED APPLICATIONS

This application is a divisional of U.S. application Ser. No. 14/880,755, filed Oct. 12, 2015, which claims priority from Japanese Application No. 2014-216429, filed Oct. 23, 2014, the entire contents of which are incorporated herein by reference.

FIELD

The present invention relates to, in pharmaceutical and food fields, an alkyl cellulose exhibiting high formability when added even in a small amount and a solid preparation comprising the alkyl cellulose.

BACKGROUND

In pharmaceutical and food fields, examples of a method of producing a solid preparation, particularly a tablet, include a dry direct tableting method comprising the steps of mixing a drug and an additive and tableting the resulting mixture as it is, and a wet granulation tableting method comprising the steps of granulating a mixture of a drug and an additive in the presence of a binder solution or a proper solvent such as water, drying the resulting granules, and tableting the dried granules. When the drug or the additive has poor fluidity or formability in the dry direct tableting method, for example, a dry granulation tableting method comprising the steps of subjecting the mixture to roll compression (dry granulation), crushing and then tableting may be employed. In the wet granulation tableting method, an agitating granulator or a fluidized bed granulator may be used.

The dry direct tableting method has been employed frequently in recent years because it can be used even when a drug is sensitive to water or because its simple process facilitates process control. However, compared with the wet granulation tableting method, the dry direct tableting method usually requires a larger amount of the additive in order to secure formability. Examples of the additive having high formability include crystalline cellulose having high formability (JP 06-316535A), hydroxyalkyl cellulose fine particles (WO 2011/065350A), and low-substituted hydroxypropyl cellulose having high formability and high fluidity (JP 2010-254756A).

On the other hand, there is a recent tendency of reducing the size of tablet to make it easier to swallow and therefore decreasing an amount of additive such as a binder. Accordingly, a binder capable of enhancing the hardness of the tablet when added even in a small amount is demanded.

SUMMARY

The additive described in JP 06-316535A, however, cannot be used for a solid preparation or small-sized tablet having high drug content because the amount of the additive has to be increased to secure formability. The additive described in WO 2011/065350A is excellent in formability but inferior in disintegration. The additive described in JP 2010-254756A is excellent in disintegration but does not have satisfactory formability. Thus, in the conventional technology, it is difficult to secure high formability without sacrificing disintegration when the amount of the additive is small.

With the foregoing in view, the invention has been made. An object of the invention is to provide an alkyl cellulose which is excellent in formability even when a small amount thereof is added and which does not remarkably delay disintegration; a solid preparation comprising the alkyl cellulose; and a method for producing the solid preparation.

With a view to achieving the above-mentioned object, the present inventors have proceeded with an extensive investigation. As a result, it has been found that the object can be achieved by using the alkyl cellulose having a specified specific surface area, leading to completion of the invention.

In an aspect of the invention, there are provided an alkyl cellulose for use in tableting, the alkyl cellulose having a specific surface area of from 0.5 to 10.0 $m^2/g$ as measured by the BET method and a solid preparation comprising the alkyl cellulose for use in tableting. In another aspect of the invention, there is also provided a method for producing an alkyl cellulose for use in tableting, the alkyl cellulose having a specific surface area of from 0.5 to 10.0 $m^2/g$ as measured by the BET method, and the method comprising the steps of: bringing pulp into contact with an alkali metal hydroxide solution to obtain alkali cellulose, reacting the alkali cellulose with an etherifying agent to obtain a first alkyl cellulose, pulverizing g the first alkyl cellulose, and depolymerizing the pulverized first alkyl cellulose through hydrolysis in the presence of an acid catalyst or through oxidative decomposition in the presence of an oxidant to obtain a second alkyl cellulose. In a further aspect of the invention, there is also provided a method for producing a solid preparation comprising: respective steps of the method for producing an alkyl cellulose for use in tableting and a step of tableting a mixture or granulated product comprising a drug and the produced alkyl cellulose for use in tableting by a dry direct tableting method or a dry granulation tableting method.

According to the present invention, since the alkyl cellulose exhibits high formability, the alkyl cellulose can enhance tablet hardness when tablets are produced by a dry direct tableting method or a dry granulation tableting method. In particular, it is effective for a formulation in which the amount of an additive is limited, for example, a formulation in which drug content should be increased; a formulation for a small-sized tablet; or a formulation for a granule-containing tablet which has to be produced at a low tableting pressure. In addition, since the alkyl cellulose exhibits high formability, flakes are available in a high yield during dry granulation, and the resulting flakes is re-pulverized to produce granules or fine granules in the presence of a reduced amount of fine powder.

DETAILED DESCRIPTION

The invention will hereinafter be described more specifically.

The alkyl cellulose has a specific surface area, as measured by the BET (BET multipoint) method, of from 0.5 to 10.0 $m^2/g$, preferably from 0.5 to 7.0 $m^2/g$, more preferably from 1.0 to 7.0 $m^2/g$, still more preferably from 1.2 to 7.0 $m^2/g$, particularly preferably 1.2 to 2.0 $m^2/g$. An alkyl cellulose having a specific surface area of less than 0.5 $m^2/g$ cannot exhibit desired formability. An alkyl cellulose having a specific surface area of more than 10.0 $m^2/g$ has deteriorated miscibility with a drug or deteriorated fluidity during production of a tablet.

The specific surface area can be analyzed using the BET (BET multipoint) method, being based on low-temperature low-humidity physical adsorption of an inert gas, and comprising the step of adsorbing a molecule having a known adsorption occupation area on the surfaces of sample powder particles at a temperature of liquid nitrogen for determining the specific surface area of the sample from the adsorption amount. It can be measured, for example, in accordance with "Method 2: The volumetric method" of "Specific Surface Area by Gas Adsorption" in General Tests described in the Japanese Pharmacopoeia 16th Edition by using an automated specific surface area and pore distribution analyzer "TriStar II 3020" (product of Micromeritics).

The viscosity at 20° C. of a 2% by weight aqueous solution of the alkyl cellulose is preferably from 1 to 15 mPa·s, more preferably from 2 to 8 mPa·s, still more preferably from 2 to 6 mPa·s, particularly preferably from 2.5 to 4.5 mPa·s. An alkyl cellulose having a viscosity of less than 1 mPa·s may not be obtained easily in the depolymerization step. An alkyl cellulose having a viscosity of more than 15 mPa·s may have poor disintegration and also have poor formability so that it may not have tablet hardness enhanced.

As described in JP 06-316535A or WO 2011/065350A, it is known that a polymer having a lower polymerization degree (i.e. a lower viscosity) usually has lower formability. However, the present inventors have found that surprisingly, an alkyl cellulose having a lower polymerization degree is superior in formability. It is presumed that an alkyl cellulose having a lower viscosity, that is, a lower polymerization degree, is apt to undergo rearrangement of molecular chains so that easy plastic deformation thereof during compression improves formability, and increases tablet hardness.

When the viscosity at 20° C. of a 2% by weight aqueous solution of the alkyl cellulose is equal to or more than 600 mPa·s, it can be measured using a rotational viscometer in accordance with "Viscosity Determination" in General Tests described in the Japanese Pharmacopoeia 16th Edition. When the viscosity at 20° C. of a 2% by weight aqueous solution of the alkyl cellulose is less than 600 mPa·s, it can be measured using an Ubbelohde-type viscometer in accordance with "Viscosity measurement by capillary tube viscometer" in General Tests described in the Japanese Pharmacopoeia 16th Edition.

The alkyl cellulose has an average particle size of preferably from 1 to 120 µm, more preferably from 1 to 70 µm, still more preferably from 10 to 70 µm, still more preferably from 10 to 50 µm, particularly preferably from 10 to 30 µm. An alkyl cellulose having an average particle size of less than 1 µm may have deteriorated miscibility with a drug or deteriorated fluidity during production of tablets. An alkyl cellulose having an average particle size of more than 120 µm may not secure an adequate specific surface area so that it may not have desired formability.

The average particle size is a volume-based average particle size and as described, for example, in page 88 of "Kaitei Zoho Funtai Bussei Zusetsu (revised and enlarged edition, Physical Properties of Powder with Illustrations" edited by The Society of Powder Technology, Japan, and The Association of Powder Process Industry and Engineering, JAPAN, published by Nikkei Gijutsu Tosho Co., Ltd., 1985, it is calculated using the formula: $\{\Sigma(nD^3)/\Sigma n\}^{1/3}$, wherein D is a particle diameter, n is the number of particles having the particle diameter, and $\Sigma n$ is a total number of particles. The term "$D_{50}$" means a particle size (i.e. average particle size) when the cumulative particle-size distribution is 50%. The average particle size can be measured using a dry laser diffraction method. For example, a volume-based average particle size can be determined from a diffraction intensity obtained by irradiating a laser light to a powder sample jetted by compressed air, as in the method using "Mastersizer 3000" (trade name) of Malvern Instruments/England or HELOS system of Sympatec GmbH/Germany.

The alkyl cellulose has a loose bulk density of preferably from 0.01 to 0.50 g/mL, more preferably from 0.03 to 0.50 g/mL, still more preferably from 0.1 to 0.50 g/mL, still more preferably from 0.2 to 0.4 g/mL. An alkyl cellulose having a loose bulk density of less than 0.01 g/mL may have deteriorated miscibility with a drug or deteriorated fluidity during production of tablets. An alkyl cellulose having a loose bulk density of more than 0.5 g/mL may have deteriorated formability.

The term "loose bulk density" means a bulk density in a loosely filled state and is determined by the method comprising the steps of: allowing a sample to pass through JIS 22-mesh sieve (opening: 710 µm), uniformly feeding the sample into a cylindrical vessel being made of a stainless steel and having a diameter of 5.03 cm and a height of 5.03 cm (capacity: 100 ml) from 23 cm above the vessel, leveling off the top surface of the sample, and then weighing the remaining sample.

The alkyl cellulose is a nonionic polymer in which one or more of the hydroxyl groups on the glucose ring of the cellulose have been etherified. Examples of the alkyl cellulose include methyl cellulose and ethyl cellulose. Of these, methyl cellulose is particularly preferred from the standpoint of formability and disintegration.

The degree of substitution of the alkyl cellulose is not particularly limited. For example, methyl cellulose has the degree of methoxy substitution of preferably from 26.0 to 33.0% by weight, more preferably from 27.5 to 31.5% by weight. The degree of methoxy substitution can be measured using a method based on the determination method of the degree of substitution of methyl cellulose described in The Japanese Pharmacopoeia 16th Edition.

Examples of a substance analogous to the alkyl cellulose include hydroxyalkylalkyl celluloses such as hydroxypropylmethyl cellulose. The present inventors have found that a tablet comprising the alkyl cellulose in accordance with the invention has a shorter disintegration time than the tablet comprising a hydroxyalkylalkyl cellulose.

It is generally known that when a tablet containing a water-soluble polymer disintegrates by the saliva, water or the like in the oral cavity, the water-soluble polymer dissolves therein to generate viscosity for preventing water from penetrating into the tablet, thereby delaying the disintegration time. Methyl cellulose and hydroxypropylmethyl cellulose are insoluble in a high temperature solvent, but become soluble as the solvent temperature decreases. Hydroxypropylmethyl cellulose dissolves at 50° C. or lower, while according to invention, the alkyl cellulose such as methyl cellulose has no hydroxyalkyl group so that a dissolution temperature thereof is lower than that of the hydroxyalkylalkyl cellulose. It is therefore presumed that since the alkyl cellulose does not dissolve in a test solution of body temperature equivalent 37° C. at which disintegration time of tablets is measured, the alkyl cellulose does not generate viscosity, thereby not delaying the disintegration time.

Next, a solid preparation comprising the alkyl cellulose will be explained.

Since the alkyl cellulose has high formability, addition of the alkyl cellulose even in a small amount can enhance the tablet hardness when tablets are produced by the dry direct tableting method or the dry granulation tableting method. The meaning of the term "small" in the "small amount" differs depending on the weight or shape of the tablet or a kind of the drug contained therein. The alkyl cellulose content in the solid preparation is preferably 20% by weight or less, more preferably 10% by weight or less, still more preferably 5% by weight or less. When the alkyl cellulose content is more than 20% by weight, a disintegration time may be deteriorated although tablet hardness may increase. The lower limit of the alkyl cellulose content differs depending on the weight or shape of the tablet or a kind of the drug contained therein. The alkyl cellulose content is preferably 0.1% by weight or more, more preferably 1% by weight or more. When the content is below 0.1% by weight, desired formability may not be achieved.

Next, a method for producing the alkyl cellulose will be described.

Pulp and an alkali metal hydroxide solution are brought into contact with each other in a conventional method to obtain an alkali cellulose. The pulp may be in sheet form or chip form. The pulp is preferably in powder form obtained by pulverization with a pulverizer. The step of bringing pulp into contact with an alkali metal hydroxide solution is preferably carried out in a reactor having an internal stirring structure.

The alkali cellulose thus obtained is reacted with an etherifying agent in a conventional method to obtain a first (high-polymerization-degree, pre-depolymerization) alkyl cellulose.

The etherifying agent useful for producing the first alkyl cellulose is known and not particularly limited. Examples of the etherifying agent include an alkylating agent such as methyl chloride.

The first alkyl cellulose obtained by the etherification reaction may be optionally purified or dried in a conventional method.

A purification method or an apparatus used for the purification is not particularly limited. It is preferably a washing method or a washing apparatus using preferably water, more preferably hot water (preferably of from 85 to 100° C.).

A drying method or an apparatus used for drying is not particularly limited. It is preferably a method or an apparatus capable of setting the temperature of the first alkyl cellulose during drying at from 40 to 80° C.

The viscosity at 20° C. of a 2% by weight aqueous solution of the first alkyl cellulose obtained after the optional purification and drying steps is not particularly limited. It is preferably more than 20 mPa·s, more preferably from 50 to 100000 mPa·s, still more preferably from 100 to 10000 mPa·s. When the viscosity at 20° C. of a 2% by weight aqueous solution of the first alkyl cellulose is equal to or more than 600 mPa·s, it can be measured using a single cylinder-type rotational viscometer in accordance with "Viscosity measurement by rotational viscometer" in General Tests described in the Japanese Pharmacopoeia 16th Edition. When the viscosity is less than 600 mPa·s, it can be measured using an Ubbelohde-type viscometer in accordance with "Viscosity measurement by capillary tube viscometer" in General Tests described in the Japanese Pharmacopoeia 16th Edition.

The first alkyl cellulose is, after the optional purification and drying steps, pulverized into particles having an average particle size of preferably from 1 to 200 μm, more preferably from 10 to 200 μm, still more preferably from 10 to 120 μm in order to satisfy the specific surface area of the alkyl cellulose obtained as a final product. After the pulverization, the resulting particles may be optionally classified through a sieve having a predetermined opening size to control the specific surface area.

A pulverization method or an apparatus to be used for the pulverization is not particularly limited. Examples of the apparatus preferably include an impact grinder such as "Turbo Mill" (product of Turbo Kogyo), "PPSR" (product of Pallmann Industries), "Victory Mill" (product of Hosokawa Micron), "Jet Mill" (product of Nippon Pneumatic), "ACM Pulverizer" (product of Hosokawa Micron) and "Micron Jet" (product of Hosokawa Micron), and a compaction grinder such as a vibration mill, a ball mill, a roller mill and a beads mill from the standpoint of obtaining a high specific surface area.

Next, the first alkyl cellulose is depolymerized to obtain a second (low-polymerization-degree, post-depolymerization) alkyl cellulose. Further improvement in formability can be expected from the depolymerization of decreasing a polymerization degree. The depolymerization may be carried out through hydrolysis in the presence of an acid catalyst or through oxidative decomposition in the presence of an oxidant. It is preferably carried out through hydrolysis in presence of an acid catalyst.

Preferred examples of an acid to be used for the depolymerization through hydrolysis in the presence of an acid catalyst include an inorganic acid such as hydrochloric acid, sulfuric acid, nitric acid and phosphoric acid. The acid may be used alone or in combination of two or more.

The acid to be added to the system may be in a gas form or a solution form. It is preferably in a solution form. The weight of the acid to be added is from 0.1 to 3.0% by weight, preferably from 0.15 to 1.5% by weight relative to the weight of the alkyl cellulose.

An internal temperature during the depolymerization is not particularly limited. It is preferably from 50 to 130° C., more preferably from 60 to 110° C., still more preferably from 60 to 90° C. The depolymerization time is preferably selected in consideration of the respective viscosities at 20° C. of 2% by weight aqueous solutions of the first alkyl cellulose (i.e. the pre-depolymerization alkyl cellulose) and the second alkyl cellulose (i.e. the post-depolymerization alkyl cellulose), and depolymerization operation conditions.

The viscosity of the 2% by weight aqueous solution of the second alkyl cellulose thus obtained after depolymerization is preferably from 1 to 15 mPa·s.

When the second alkyl cellulose thus obtained has a specific surface area outside the range of the invention, an alkyl cellulose having the specific surface area of the invention can be obtained by further pulverizing the second alkyl cellulose. The specific surface area may be controlled by classifying the pulverized particles, for example, through a sieve having a predetermined opening size. A pulverization method or a pulverizer used for the pulverization is not particularly limited. The above-mentioned pulverizer or the like can be used. The sieve to be used for the classification is not particularly limited. The sieves such as a JIS 200-mesh sieve (opening: 75 μm), JIS 235-mesh sieve (opening: 63 μm), JIS 330-mesh sieve (opening: 45 μm) and JIS 390-mesh sieve (opening: 38 μm) are preferred.

Next, a method for producing a solid preparation comprising the obtained alkyl cellulose for use in tableting will be explained.

A solid preparation can be obtained by tableting or granulating the alkyl cellulose for use in tableting, together with a drug and a various additive commonly usable in this field including an excipient, a disintegrant, a binder, an aggregation-preventing agent and a solubilizing agent for a pharmaceutical compound. Examples of the solid preparation include a tablet, a granule, a powder and a capsule. The solid preparation can be used as an orally disintegrating tablet, which has been investigated actively in recent years.

The tablet can be produced by any of a dry direct tableting method, a dry granulation tableting method, a wet agitation granulation tableting method and a fluidized bed granulation tableting method and others. Of these, the dry direct tableting method and the dry granulation tableting method are particularly preferred from the standpoint of each using the alkyl cellulose without dissolution thereof.

The dry direct tableting method is the method of tableting a mixture comprising a drug and the alkyl cellulose for use in tableting, as well as, for example, an optional excipient, an optional disintegrant and/or an optional lubricant, the mixture having been obtained by dry mixing. The dry direct tableting method does not comprise a granulation step so that it can simplify the manufacturing process and is a highly productive method.

The dry granulation tableting method is the method of tableting granules comprising a drug and the alkyl cellulose for use in tableting, as well as, for example, an optional excipient, an optional disintegrant and/or an optional lubricant, the granules having been obtained by compression granulation. The dry granulation tableting method is effective for a drug sensitive to water or a solvent. The compression granulation product can be obtained, for example, through roller compression using a compaction granulator such as a roller compactor. The roller pressure is variable depending on, for example, the physical properties of the powders. The roller pressure is preferably from 1 to 30 MPa, more preferably from 2 to 12 MPa and the rotation speed of the roller is preferably from 1 to 50 rpm, more preferably from 2 to 20 rpm. The rotation speed of a screw is preferably from 1 to 100 rpm, more preferably from 2 to 50 rpm. Flakes obtained through roller compression are subjected to pulverization and sizing by using a pulverizer or crusher such as Comill, a quick mill or a power mill, into granules having desired particle sizes for tableting.

The alkyl cellulose for tableting can also be used for orally disintegrating tablets which have been investigated actively in recent years.

According to the invention, a drug to be used for producing a solid preparation comprising the alkyl cellulose is not particularly limited insofar as it is orally administrable. Examples of the drug include drugs for the central nervous system, drugs for the circulatory system, drugs for the respiratory system, drugs for the digestive system, antibiotics, antitussives/expectorants, antihistamines, analgesic antipyretic anti-inflammatory drugs, diuretics, autonomic drugs, antimalarial drugs, antidiarrheal agents, psychotropic drugs, and vitamins and derivatives thereof.

Examples of the drugs for the central nervous system include diazepam, idebenone, aspirin, ibuprofen, paracetamol, naproxen, piroxicam, dichlofenac, indomethacin, sulindac, lorazepam, nitrazepam, phenytoin, acetaminophen, ethenzamide, ketoprofen and chlordiazepoxide.

Examples of the drugs for the circulatory system include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, propranolol hydrochloride and alprenolol hydrochloride.

Examples of the drugs for the respiratory system include amlexanox, dextromethorphan, theophilline, pseudo-ephedrine, salbutamol and guaiphenesin.

Examples of the drugs for the digestive system include benzimidazole-based drugs having anti-ulcer action such as 2-[(3-methyl-4-(2,2,2-trifluoroethoxy)-2-pyridyl)methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotics include talampicillin hydrochloride, bacampicillin hydrochloride, cephaclor and erythromycin.

Examples of the antitussives/expectorants include noscapine hydrochloride, carbetapentane citrate, dextromethorphan hydrobromide, isoaminile citrate and dimemorfan phosphate.

Examples of the antihistamines include chlorpheniramine maleate, diphenhydramine hydrochloride and promethazine hydrochloride.

Examples of the analgesic antipyretic and anti-inflammatory drugs include ibuprofen, diclofenac sodium, flufenamic acid, sulpyrine, aspirin and ketoprofen.

Examples of the diuretics include caffeine.

Examples of the autonomic drugs include dihydrocodeine phosphate, methylephedrine dl-hydrochloride, atropine sulfate, acetylcholine chloride and neostigmine.

Examples of the antimalarial drugs include quinine hydrochloride.

Examples of the antidiarrheal agents include loperamide hydrochloride.

Examples of the psychotropic drugs include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate and tranexamic acid.

Examples of the excipient include saccharides such as sucrose, lactose and glucose; sugar alcohols such as mannitol, sorbitol and erythritol; starches; crystalline cellulose; calcium phosphate; and calcium sulfate.

Examples of the binder include polyvinyl alcohol, polyacrylic acid, polymethacrylic acid, polyvinylpyrrolidone, glucose, sucrose, lactose, maltose, dextrin, sorbitol, mannitol, macrogols, gum arabic, gelatin, agar, starches, crystalline cellulose and low-substituted hydroxypropyl cellulose.

Examples of the disintegrant include low-substituted hydroxypropyl cellulose, carmellose or a salt thereof, croscarmellose sodium, carboxymethyl starch sodium, crospovidone, crystalline cellulose and crystalline cellulose carmellose sodium.

Examples of the lubricant and the aggregation-preventing agent include talc, magnesium stearate, calcium stearate, colloidal silica, stearic acid, waxes, hydrogenated oils, polyethylene glycols and sodium benzoate.

Examples of the solubilizing agent for a pharmaceutical compound include organic acids such as fumaric acid, succinic acid, malic acid and adipic acid.

EXAMPLES

The invention will hereinafter be described more specifically on basis of Examples and Comparative Examples. However, it should not be construed that the invention is limited to or by Examples. There can be modifications in various ways by those skilled in the art without departing from the technical concept of the invention.

Example 1

An internal stirring type pressure reactor was charged with 6.0 kg, in terms of cellulose content, of powdery pulp. After vacuuming and nitrogen purge, 14.1 kg of a 49% by weight aqueous sodium hydroxide solution was added thereto and stirred to obtain alkali cellulose. Then, 11.9 kg of methyl chloride was added thereto and reacted to obtain a methyl cellulose reaction product. The reaction product thus obtained was washed, dried, ground using a high-speed rotating impact grinding mill, Victory Mill, equipped with a screen of 0.3-mm openings, and filtered through a sieve with 150-μm openings to obtain first methyl cellulose (high-polymerization-degree, pre-depolymerization). The first methyl cellulose had a degree of methoxy substitution of 29% by weight.

To the first (high-polymerization-degree, pre-depolymerization) methyl cellulose was added a 10% by weight aqueous hydrochloric acid solution in an amount equivalent of 0.3% by weight of HCl relative to the amount of the methyl cellulose. The internal temperature was regulated to 80° C. and depolymerization was carried out for 70 minutes to obtain second (low-polymerization-degree, post-depolymerization) methyl cellulose. The specific surface area, viscosity at 20° C. of a 2% by weight aqueous solution, average particle size, and loose bulk density of the resulting powder are shown in Table 1.

After adjustment of the water content of the second methyl cellulose thus obtained to 2.5 to 3.5% in a 33% RH desiccator, the resulting second methyl cellulose was compressed and tableted at compression pressure of 50 MPa into tablets having a tablet weight of 480 mg by using a single-punch tableting machine (trade name "Tableting tester", product of Sankyo Biotech). The punch was a flat punch having a diameter of 11.3 mm and having a flat contact surface. The hardness of the tablets thus obtained is shown in Table 1.

In order to have comparison with the below-mentioned hardness-unmeasurable samples due to high hardness of the tablets, the hardness was also measured for the tablets obtained at lower tableting pressure after the adjustment of the water content of the second methyl cellulose. More specifically, the second methyl cellulose was compressed and tableted at compression pressure of 30 MPa into tablets having a tablet weight of 450 mg by using a desk-top type tableting machine (trade name "HANDTAB-200", product of Ichihashi Seiki). The punch was a flat punch having a diameter of 12 mm and having a flat contact surface. The hardness of the tablets thus obtained is also shown in Table 1.

The term "water content" as used herein means a value calculated in accordance with the following equation by using dry matter content determined by the method specified in JIS P8203:1998 Determination of Dry Matter Content for Pulp.

Water content (%)=100−(dry matter content) (%)

In the above equation, the dry matter content is a ratio (%) of the weight of the sample dried at 105±2° C. until reaching a constant value as the weight of the sample to the weight of the sample before dried.
(Measurement Conditions)

The specific surface area by the BET (BET multipoint) method was measured through a gas adsorption method (adsorption gas: nitrogen, refrigerant: liquid nitrogen) by using an automated specific surface area and pore distribution analyzer "TriStar II 3020" (trade name; product of Micromeritics) in accordance with the "Method 2: The volumetric method" of "Specific Surface Area by Gas Adsorption" in General Tests described in the Japanese Pharmacopoeia 16th Edition, while keeping a relative pressure ($P/P_0$), wherein $P_0$ represents a saturated vapor pressure and P represents a measured equilibrium pressure, within a range of from 0.05 to 0.30. About 0.5 to 2 g, depending on the loose bulk density, of a sample dried at 105° C. for 2 hours was used for the measurement.

When the viscosity at 20° C. of a 2% by weight aqueous solution was 600 mPa·s or greater, it was measured using a single cylinder-type rotational viscometer in accordance with "Viscosity measurement by rotational viscometer" in General Tests described in the Japanese Pharmacopoeia 16th Edition. When the viscosity was less than 600 mPa·s, it was measured using an Ubbelohde-type viscometer in accordance with "Viscosity measurement by capillary tube viscometer" in General Tests described in the Japanese Pharmacopoeia 16th Edition.

The average particle size was measured at dispersion pressure of 2 to 3 bars and scattering intensity of from 2 to 10% through laser diffraction (analysis: Fraunhofer approximation) by using "Mastersizer 3000" (trade name; product of Malvern Instruments).

The loose bulk density was measured using "Powder Tester PT-S" (trade name; product of Hosokawa Micron). A sample was fed uniformly into the cylindrical vessel (made of stainless steel) having a diameter of 5.03 cm and a height of 5.03 cm (capacity: 100 ml) from 23 cm above the vessel through a JIS 22-mesh sieve (opening: 710 μm) and was weighed after leveling off the top surface of the sample.

The tablet hardness was measured using a tablet hardness tester "TBH-125" (trade name; product of ERWEKA GmbH). A load was applied to the diameter direction of a tablet at a rate of 1 mm/sec and the maximum breaking strength at which the tablet was broken was measured.

Example 2

The second methyl cellulose obtained in Example 1 was ground using a high-speed rotating impact grinding mill, Victory Mill, equipped with a screen of 0.3-mm openings to obtain the intended second methyl cellulose. The physical properties of the resulting powder and tablet hardness of tablets obtained using a single-punch tableting machine and a desk-top type tableting machine in the same manner as in Example 1 are shown in Table 1.

Example 3

The second methyl cellulose obtained in Example 2 was filtered through a sieve of 38-μm openings to obtain intended second methyl cellulose. The physical properties of the resulting powder and tablet hardness of tablets obtained using a single-punch tableting machine and a desk-top type tableting machine in the same manner as in Example 1 are shown in Table 1.

Example 4

The second methyl cellulose obtained in Example 1 was ground using an airflow type impact grinding mill "Jet Mill" (product of Nippon Pneumatic) at grind pressure of 0.35 MPa, clearance of 20 mm in the classification zone and the louver size of "Large" to obtain the intended second methyl cellulose. The physical properties of the resulting powder and tablet hardness of tablets obtained using a single-punch tableting machine and a desk-top type tableting machine in the same manner as in Example 1 are shown in Table 1.

Example 5

In the same manner as in Example 1 except that depolymerization time of the first (high-polymerization-degree, pre-depolymerization) methyl cellulose obtained in Example 1 was changed to 30 minutes, the intended second methyl cellulose was obtained. The physical properties of the resulting powder and tablet hardness of tablets obtained using a single-punch tableting machine and a desk-top type tableting machine in the same manner as in Example 1 are shown in Table 1.

Example 6

In the same manner as in Example 1 except that depolymerization time of the first (high-polymerization-degree, pre-depolymerization) methyl cellulose obtained in Example 1 was changed to 190 minutes, the intended second methyl cellulose was obtained. The physical properties of the resulting powder and tablet hardness of tablets obtained using a single-punch tableting machine and a desk-top type tableting machine in the same manner as in Example 1 are shown in Table 1.

Example 7

In the same manner as in Example 4 except for using grind pressure of 0.45 MPa and clearance of 35 mm in the classification zone, the intended second methyl cellulose was obtained. The physical properties of the resulting powder and tablet hardness of tablets obtained using a single-punch tableting machine and a desk-top type tableting machine in the same manner as in Example 1 are shown in Table 1. The hardness of the tablets obtained using a single-punch tableting machine was so high that the hardness was beyond the measurement limit of 500N and thus unmeasureable.

Example 8

In the same manner as in Example 4 except for using grind pressure of 0.5 MPa, clearance of 35 mm in the classification zone and the louver size of "Small", the intended second methyl cellulose was obtained. The physical properties of the resulting powder and tablet hardness of tablets obtained using a single-punch tableting machine and a desk-top type tableting machine in the same manner as in Example 1 are shown in Table 1. The hardness of the tablets obtained using a single-punch tableting machine was so high that the hardness was beyond the measurement limit of 500N and thus unmeasureable.

Comparative Example 1

The methyl cellulose reaction product was obtained in the same manner as in Example 1, washed, dried and ground using a high-speed rotating impact grinding mill, Victory Mill, equipped with 0.5-mm openings. The resulting particles were filtered through a sieve of 35 μm to obtain the first (high-polymerization-degree, pre-depolymerization) methyl cellulose. The first (high-polymerization-degree, pre-depolymerization) methyl cellulose thus obtained was depolymerized in the same manner as in Example 1 to obtain the second (low-polymerization-degree, post-depolymerization) methyl cellulose. The physical properties of the resulting powder and tablet hardness of tablets obtained using a single-punch tableting machine and a desk-top type tableting machine in the same manner as in Example 1 are shown in Table 1.

TABLE 1

| | powder properties | | | | tablet hardness | |
|---|---|---|---|---|---|---|
| | specific surface area ($m^2$/g) | viscosity (mPa · s) | average particle size (μm) | loose bulk density (g/mL) | single-punch tableting machine (N) | desk-top tableting machine (N) |
| Example 1 | 0.75 | 4.18 | 52.1 | 0.27 | 215 | 136 |
| Example 2 | 1.09 | 4.24 | 32.0 | 0.24 | 249 | 151 |
| Example 3 | 1.32 | 3.61 | 22.0 | 0.25 | 283 | 167 |
| Example 4 | 1.72 | 3.45 | 20.8 | 0.22 | 334 | 202 |
| Example 5 | 0.86 | 6.88 | 53.0 | 0.27 | 206 | 122 |
| Example 6 | 0.81 | 2.65 | 49.0 | 0.26 | 234 | 142 |
| Example 7 | 3.57 | 4.09 | 9.4 | 0.11 | unmeasurable | 350 |
| Example 8 | 6.07 | 3.78 | 4.5 | 0.08 | unmeasurable | 404 |
| Comp. Ex. 1 | 0.44 | 4.25 | 84.2 | 0.24 | 123 | 71 |

It is evident from Table 1 that the methyl cellulose obtained in each of Examples 1 to 8 shows high formability, while the methyl cellulose obtained in Comparative Example 1 is inferior in formability. Surprisingly, even when the methyl cellulose has a specific surface area of the same level (in Examples 1, 5, and 6), the methyl cellulose has improved formability as its viscosity decreases.

Example 9

The methyl cellulose obtained in Example 3 was mixed for three minutes in a polyethylene bag with the components listed in the tablet composition below except for magnesium stearate. Then, magnesium stearate was added thereto, mixed for 30 seconds, and tableted under the following tableting conditions. The dry direct tableting method was used to obtain tablets. The tablet hardness of the tablets thus obtained and disintegration time (test liquid: water) in the Japanese Pharmacopoeia Disintegration Test were evaluated. The results are shown in Table 2.

Tablet Composition:
Acetaminophen fine powder (product of Yamamoto Chemical Ind. Co., Ltd.):
50.0 parts by weight
Lactose hydrate (trade name "Dilactose S"; product of Freund Corp.):

44.5 parts by weight
Methyl cellulose: 5.0 parts by weight
　　Light silicic anhydride: 0.5 parts by weight
　　Magnesium stearate: 0.5 parts by weight
Tableting Conditions
　　Tableting machine: rotary tableting machine (trade name "VIRGO"; product of Kikusui Seisakusho)
　　Tablet size: 200 mg/tablet, 8 mm-D, 12 mm-R
　　Tableting pressure: 10 kN
　　Tableting speed: 20 rpm Example 10

In the same manner as in Example 9 except for use of the methyl cellulose obtained in Example 4, tablets were produced through the dry direct tableting method. The tablet hardness of the tablets thus obtained and disintegration time (test liquid: water) in the Japanese Pharmacopoeia Disintegration Test were evaluated. The results are shown in Table 2.

Comparative Example 2

In the same manner as in Example 9 except for use of the methyl cellulose obtained in Comparative Example 1, tablets were produced by the dry direct tableting method. The tablet hardness of the tablets thus obtained and disintegration time (test liquid: water) in the Japanese Pharmacopoeia Disintegration Test were evaluated. The results are shown in Table 2.

TABLE 2

|  | tablet hardness (N) | disintegration time (minutes) |
| --- | --- | --- |
| Example 9 | 68.5 | 9.6 |
| Example 10 | 73.2 | 9.1 |
| Comp. Ex. 2 | 40.3 | 6.5 |

It is evident from Table 2 that the tablets obtained in Examples 9 and 10 by the dry direct tableting method had higher tablet hardness than that of tablets obtained in Comparative Example 2. On the other hand, significant delay in disintegration time was not observed.

Example 11

Using the methyl cellulose obtained in Example 3, the powder having the following composition was dry granulated with "Roller Compactor MINI" (trade name; product of Freund Corporation) at roll pressure of 6 MPa, a roll rotation speed of 4 rpm, and a screw rotation speed of 5 rpm.
Composition of Ground Powders
　　Acetaminophen fine powder (product of Yamamoto Chemical Ind. Co., Ltd.):
　　10.0 parts by weight
　　Lactose hydrate (trade name "Pharmatose 200M"; product of DFE Pharma):
　　79.0 parts by weight
　　Methyl cellulose: 10.0 parts by weight
　　Light silicic anhydride: 0.5 parts by weight
　　Magnesium stearate: 0.5 parts by weight
To the granulated product was further added 0.5 parts by weight of magnesium stearate. The resulting mixture was mixed for 30 seconds, and tableted under the following tableting conditions to obtain tablets. The tablet hardness of the tablets thus obtained is shown in Table 3.
Tableting Conditions
　　Tableting machine: rotary tableting machine (trade name "VIRGO"; product of Kikusui Seisakusho)
　　Tablet size: 200 mg/tablet, 8 mm-D, 12 mm-R
　　Tableting pressure: 10 kN
　　Tableting speed: 20 rpm Example 12

After dry granulation in the same manner as in Example 11 except for use of the methyl cellulose obtained in Example 4, the granulated powder was tableted into tablets. The tablet hardness of the tablets thus obtained is shown in Table 3.

Comparative Example 3

After dry granulation in the same manner as in Example 11 except for use of the methyl cellulose obtained in Comparative Example 1, the granulated powder was tableted into tablets. The tablet hardness of the tablets thus obtained is shown in Table 3.

TABLE 3

|  | tablet hardness (N) |
| --- | --- |
| Example 11 | 50.5 |
| Example 12 | 56.9 |
| Comp. Ex. 3 | 34.2 |

It is evident from Table 3 that the preparations obtained in Examples 11 and 12 by dry granulation tableting method had tablet hardness higher than that in Comparative Example 3.

The invention claimed is:

1. An alkyl cellulose for use in tableting, wherein the alkyl cellulose has a specific surface area of from 0.5 to 10.0 m$^2$/g as measured by BET method.

2. The alkyl cellulose for use in tableting according to claim 1, wherein an aqueous solution comprising 2% by weight of said alkyl cellulose has a viscosity at 20° C. of from 1 to 15 mPa·s.

3. The alkyl cellulose for use in tableting according to claim 1, the alkyl cellulose having an average particle size of from 1 to 120 μm.

4. The alkyl cellulose for use in tableting according to claim 1, the alkyl cellulose having a loose bulk density of from 0.01 to 0.50 g/mL.

5. The alkyl cellulose for use in tableting according to claim 1, the alkyl cellulose being methyl cellulose.

6. A solid preparation comprising the alkyl cellulose for use in tableting according to claim 1.

7. The alkyl cellulose for use in tableting according to claim 1, wherein the specific surface area is from 1.2 to 2.0 m$^2$/g as measured by BET method.

8. The alkyl cellulose for use in tableting according to claim 2, wherein the viscosity at 20° C. is from 2.5 to 4.5 mPa·s.

9. The alkyl cellulose for use in tableting according to claim 3, wherein the average particle size is from 10 to 30 μm.

10. The alkyl cellulose for use in tableting according to claim 3, wherein the loose bulk density is from 0.2 to 0.4 g/mL.

* * * * *